United States Patent [19]

Farling

[11] 4,055,862
[45] Nov. 1, 1977

[54] HUMAN BODY IMPLANT OF GRAPHITIC CARBON FIBER REINFORCED ULTRA-HIGH MOLECULAR WEIGHT POLYETHYLENE

[75] Inventor: Gene M. Farling, Warsaw, Ind.
[73] Assignee: Zimmer USA, Inc., Warsaw, Ind.
[21] Appl. No.: 651,706
[22] Filed: Jan. 23, 1976
[51] Int. Cl.² .............................................. A61F 1/24
[52] U.S. Cl. ...................................... 3/1.91; 3/1.911; 3/1.912; 128/92 C; 264/122; 264/126
[58] Field of Search ............................ 3/1, 1.9–1.913; 128/92 C, 92 CA

[56] References Cited

U.S. PATENT DOCUMENTS

| | | | |
|---|---|---|---|
| 3,698,017 | 10/1972 | Scales et al. | 3/1.912 |
| 3,728,742 | 4/1973 | Averill et al. | 3/1.911 |
| 3,869,731 | 3/1975 | Waugh et al. | 3/1.911 |
| 3,893,196 | 7/1975 | Hochman | 3/1.91 |

FOREIGN PATENT DOCUMENTS 1,902,700  8/1970  Germany .................................. 3/1.91

OTHER PUBLICATIONS

"Polymers as Bearing Materials for Total Hip Replacement: A Friction and Wear Analysis" by H. A. Amstutz, Journal of Biomedical Materials Research, vol. 3, No. 4, Dec. 1969, pp. 547–568.

"Quartz & Graphite Filament Reinforced Polymer Composites for Orthopedic Surgical Application" by S. Musikant, Journal of Biomedical Materials Symposium, vol. 1, pp. 225–235, 1971.

The Mechanical & Physical Properties of Materials by D. F. Williams (Chapter 3) Implants In Surgery (Book) by Williams & Roaf, W. B. Saunders Co. Ltd., London, 1973, pp. 89–93.

*Primary Examiner*—Ronald L. Frinks
*Attorney, Agent, or Firm*—Olson, Trexler, Wolters, Bushnell & Fosse, Ltd.

[57] ABSTRACT

A medical body implant element that is intended to experience rolling or sliding pressure during its function in the human body comprises microparticles of ultra-high molecular weight polyethylene which are fused together into a matrix. A quantity of graphitic carbon fibers of short, random lengths is disposed in intersticies of the matrix. The resultant composite is wear-resistant and substantially isotropic.

6 Claims, 10 Drawing Figures

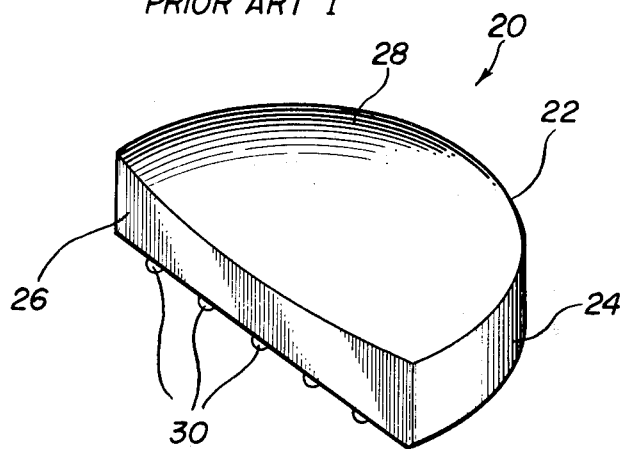
FIG. 1 PRIOR ART I
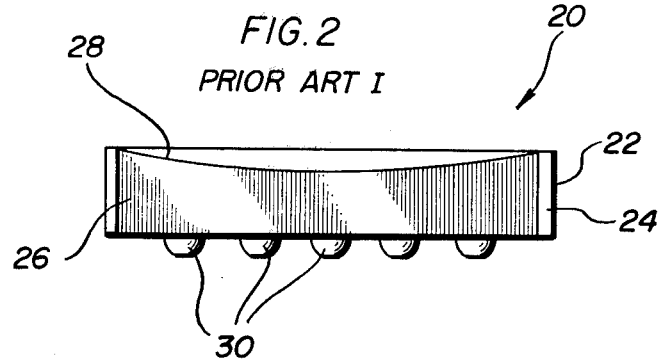
FIG. 2 PRIOR ART I
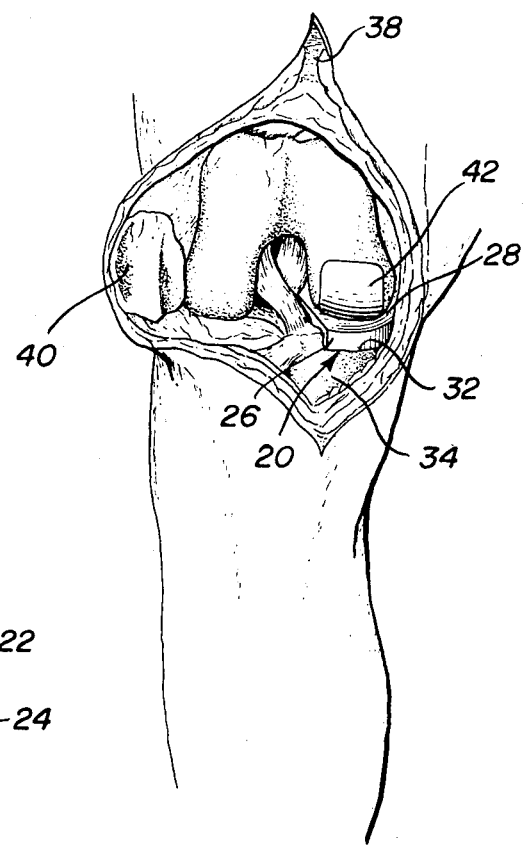
FIG. 3 PRIOR ART I
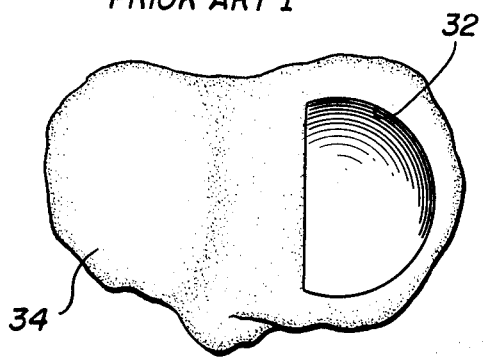
FIG. 4 PRIOR ART I
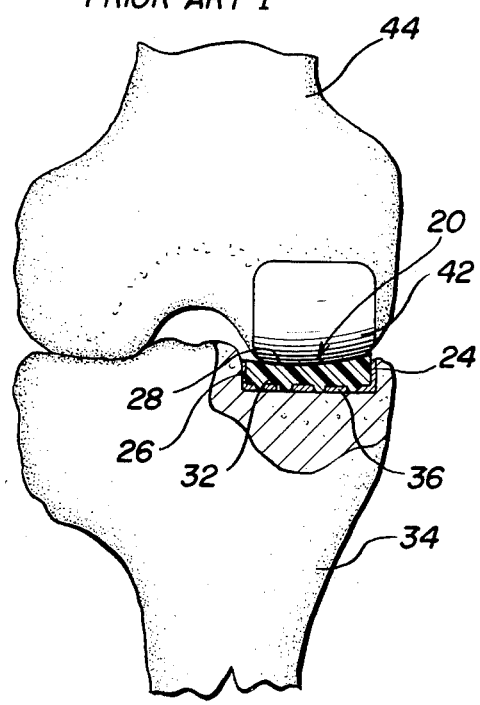
FIG. 4A PRIOR ART I

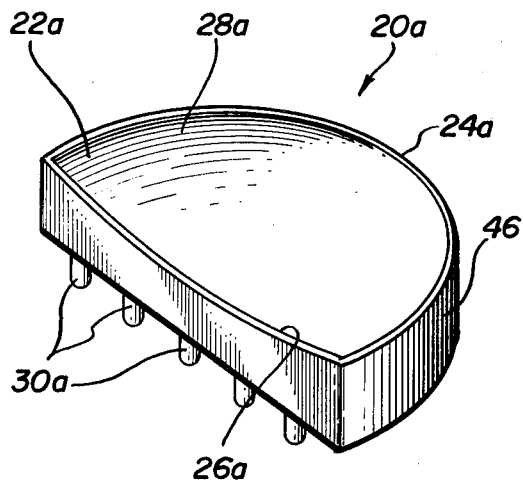
FIG. 5
PRIOR ART II
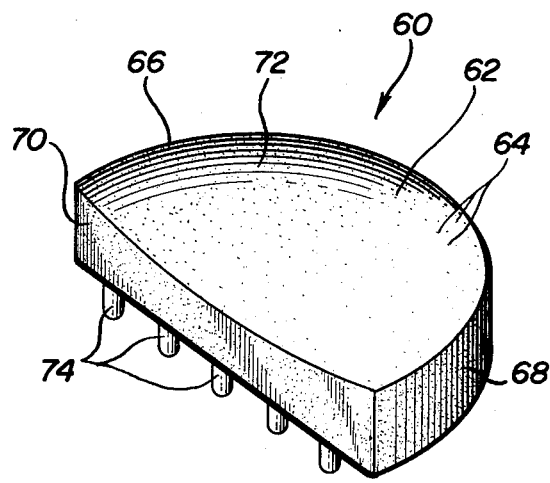
FIG. 6
INVENTION
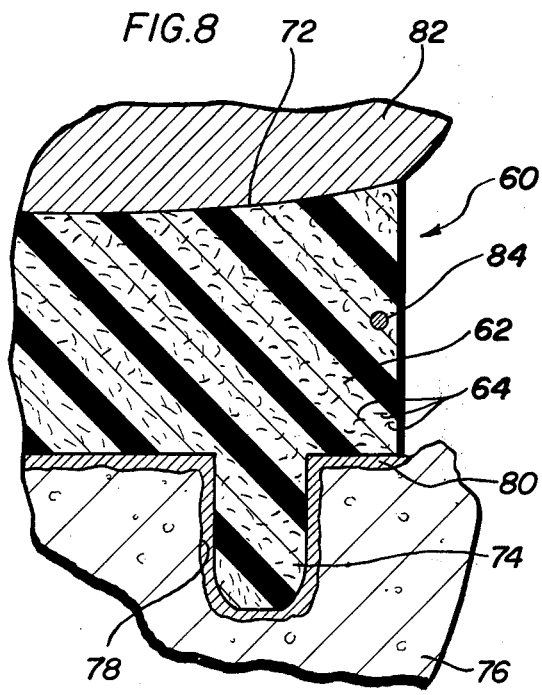
FIG. 8
FIG. 7
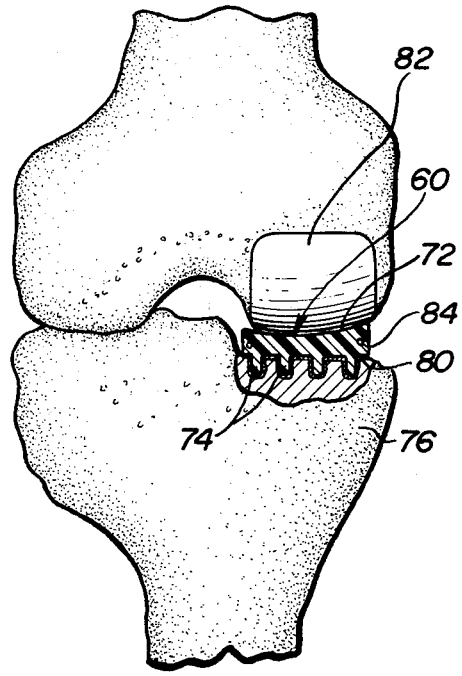
FIG. 9
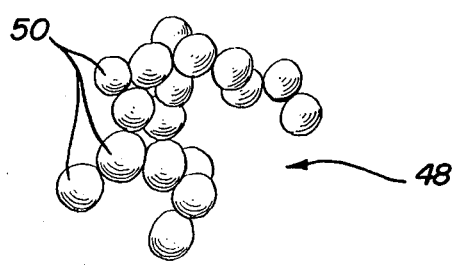

HUMAN BODY IMPLANT OF GRAPHITIC CARBON FIBER REINFORCED ULTRA-HIGH MOLECULAR WEIGHT POLYETHYLENE

BACKGROUND OF THE INVENTION

This invention relates generally to the art of medical prostheses, more particularly to human body implants, and especially to such implants that are subjected to sliding or rolling pressure or to a combination of such pressures during function in the human body.

In recent decades, the emphasis in surgical repair of functionally impaired skeletal joints has shifted from fusion of the involved joint and resultant total immobilization thereof to the implantation of synthetic joint components and even artificial, total joint assemblages. Great medical advances have been made using these implants; and the materials selected for the construction of the component parts have commonly been various metals and alloys. Polymeric materials have also been increasingly employed, especially for elements that are incident to sliding, rolling or grinding motion upon articulation of the repaired joint.

Because of their chemical inertness and low friction properties, polyethylene resins have received considerable attention as candidates for anti-friction, human body implants. However, polyethylenes have limitations in the medical environment. For example, they may release surface particles and are known to be susceptible to "cold flow" and resultant loss of intended geometry when subjected to compressive forces over extended periods of time. The higher molecular weight polyethylenes, i.e., those having molecular weights on the order of 400,000 to 600,000 and having linear characteristic, exhibit increased tendencies to incur "cold flow"; but these latter polymers display concomitantly lesser propensities toward stress cracking, after implantation. Heretofore, attempts have been made to compensate for the various deficiencies of polyethylenes by such expediencies as metallic perimeter containments and implantation in cavities prepared to leave a surrounding rim of either bone or a combination of bone and synthetic bone "cement". Undesirable complexities in fabrication and in surgery have been the consequence.

Furthermore, attempts have been made in the past to reinforce various polymers with carbon fibers. However, these efforts have been principally directed either to thermosetting, rather than thermoplastic, resins or to general mechanical, non-medical applications such as bearings, slideways, electrical housings and the like. Moreover, minimal efforts have been devoted to producing polyethylene-carbon fiber composites for medical implants, or other uses, because "fillers" of whatever nature are generally known to have very pronounced and unpredictable effects on the physical properties of polyethylene.

SUMMARY OF THE INVENTION

The present invention is based on the discoveries that ultra-high molecular weight polyethylene can be fabricated into highly useful human body implants by incorporating very short sections of graphitic carbon fibers with the resin particles and by fabricating the implants from the resin-fiber mixture using a special molding operation that results in a substantially isotropic part.

Accordingly, a general object of the present invention is to provide a new and improved medical implant.

Another object of the invention is to provide a polyethylene-based, human body implant which is resistant to "cold flow".

Yet another object of the present invention is to provide a polyethylene-based, human body implant which retains its geometry under prolonged conditions of exposure to rolling or sliding pressure or to a combination of such pressures.

Still another object of the present invention is to provide a substantially isotropic human body implant that is composed of short carbon fibers distributed in an ultrahigh molecular weight polyethylene matrix.

BRIEF DESCRIPTION OF THE DRAWINGS

In order that the principals of the present invention may be readily understood, two prior art implants and a single embodiment of the invention, applied to tibial plateau prostheses, but to which the application is not to be restricted, are shown in the accompanying drawings wherein:

FIG. 1 is an enlarged perspective view of a tibial plateau prosthesis constructed in compliance with a first prior art scheme;

FIG. 2 is a side elevational view showing the truncated face of the prosthesis of FIG. 1;

FIG. 3 is a schematic view illustrating surgical installation of the prosthesis of FIGS. 1 and 2;

FIG. 4 is a top plan view of the proximal tibia involved in the procedure of FIG. 3 and showing the tibia excavated to receive the prosthesis of FIGS. 1 and 2;

FIG. 4A is an elevational view, partially in cross-section, showing the installation of the prosthesis of FIGS. 1 and 2 in the prepared tibia;

FIG. 5 is a view similar to the showing of FIG. 1 but illustrating a second form of prior art tibial plateau prosthesis, which includes a peripheral containment member;

FIG. 6 is an enlarged perspective view of a tibial plateau prosthesis constructed in compliance with the principals of the present invention;

FIG. 7 is a view similar to the showing of FIG. 4A, but illustrating implantation of the tibial plateau prosthesis of FIG. 6;

FIG. 8 is an enlarged, fragmentary, elevational view taken in cross-section and illustrating the prosthesis of FIG. 6 installed as shown in FIG. 7; and FIG. 9 is a greatly enlarged perspective view showing a particle of ultra-high molecular weight polyethylene comprising a plurality of connected microspheres as employed as a starting material for the implant of the present invention.

DESCRIPTION OF THE DISCLOSED EMBODIMENT

The term "ultra-high molecular weight" is used herein to describe polyethylene resins having a molecular weight of greater than about 1.5 million and preferably from about two million to about four million. By comparison, ordinary polyethylene resins display molecular weights on the order of 400,000 to one million.

Furthermore, the term "fiber" as used herein is intended to refer both to single filaments and to multiple filaments entwined together into a fine yarn-like element.

Referring now in detail to the drawings, specifically to FIGS. 1 and 2, a human body implant defining a tibial plateau prosthesis and constructed in compliance with the prior art is indicated generally by the reference numeral 20. The prosthesis 20 includes a substantially half-disc- like body 22 having a cylindrical sidewall 24 that is truncated by a substantially straight, diametral face 26. The prosthesis body 22 itself is provided with a spherically concave upper surface 28, and the tibial plateau prosthesis additionally comprises a suitable number of depending protuberances 30 which are confluent with the main body 22. In compliance with the prior art, the tibial plateau prosthesis 20 is fabricated from unfilled, high density polyethylene resin which is first extruded into a rod or bar. Thereafter, individual planchets are severed from the extrusion and machined to the ultimate configuration of the prosthesis. I have found that an undesirable degree of anisotropism exists in such implants.

The prosthesis 20 is intended for use in correcting varus and valgus deformities of the tibia, and such prostheses are commonly provided in a selection of different heights to accommodate individual needs. In further accord with conventional practices, the tibial plateau prosthesis 20 is embedded in a D-shaped cavity 32 which is formed at the proximal end of the tibia 34 during surgery, as is best shown in FIGS. 3 and 4. Polymethylmethacrylate bone cement 36 is employed in installing the prosthesis 20 in the cavity 32, as is best seen in FIG. 4A; and there, it will be noted that the prosthesis 20 is deposited in the cavity 32 so that both the semicylindrical sidewall 24 and the diametral face 26 are confronted by either bone or a combination of bone and cement.

In surgery, the knee is opened through a longitudinally extending parapatellar incision 38 and the patella 40 itself is rotated laterally before the knee is flexed for excision of unwanted tissue and for preparation of the cavity 32. When the patient has recovered from surgery and the repaired knee joint is to be used in articulation, the spherical upper surface 28 of the prosthesis 20 will be engaged by a cooperating metallic implant 42 located distally of femur 44 as is shown in FIGS. 3 and 4A. As will be appreciated, the spherical surface 28 is engaged fittingly by the femoral condylar implant and serves as a journal or bearing surface for the metallic condylar implant during use of the corresponding limb. Clinical experience with prostheses such as the prosthesis 20 indicates tendencies toward wear, cracking and even surface disintegration of the polyethylene component accompanied by varying degrees of disfunction of the repaired joint.

Cold flow and resultant loss of geometry, particularly of the spherical surface 28, have also been observed in prior art polyethylene medical implant devices, such as the prosthesis 20, even when the perimeter of the implant has been contained with a surrounding rim of bone or a combination of bone and bone cement, as described with reference to FIGS. 3, 4, and 4A. Other efforts involving external containments have also proved ineffective in this regard, and one such additional prior art proposal is illustrated in FIG. 5. The embodiment of FIG. 5 incorporates elements similar to those shown in the embodiment of FIGS. 1–4A; and accordingly, like numerals have been used to designate like parts with the suffix letter "a" being employed to distinguish those elements associated with the embodiment of FIG. 5. The tibial plateau prosthesis 20a is characterized by the provision of a continuous, pre-shaped metal band 46 which encompasses the polyethylene body 22a in engagement with the semi-cylindrical sidewall 24a and the diametral face 26a.

By contrast to the prior art approaches described hereinabove, the present invention contemplates the fabrication of a medical implant element from ultra-high molecular weight polyethylene and a quantity of graphitic carbon fibers. Under certain circumstances, improvements in wear resistance of as much as 500% have been observed as compared with unmodified ultra-high molecular weight polyethylene.

In the practice of the present invention, small bodies 48 of ultra-high molecular weight polyethylene are selected to comprise agglomerates of minute particles produced by the polymerization reactor. These particles are essentially beads or spheroids 50 having diameters or major dimensions of on the order of about one to ten microns. Such a body 48 is suggested in FIG. 9; and a quantity of these bodies is mixed with up to about thirty per cent by weight of graphitic carbon fibers. The mixture is then agitated mechanically to establish uniform distribution; and an amount of the polyethylene/carbon fiber mixture is delivered to a mold. There, heat and mechanical pressure are applied to fuse the microparticles of ultra-high molecular weight polyethylene into a matrix 62, the short, random length graphitic carbon fibers 64 being concomitantly disposed in interstices of the matrix, as is best shown in FIG. 8. Because the mixture is thus compressed, rather than being caused to flow (as would occur in extrusion or transfer molding or injection molding), the graphitic carbon fibers consist essentially of a substantially unoriented array and the original, random alignment of the polyethylene molecules in the microparticles is preserved. As will be appreciated, the resultant molded, finished parts may be subsequently machined to a further configuration without altering the isotropic condition of the filled matrix material.

In compliance with preferred forms of the medical implant element of the present invention, the graphitic carbon fibers in the ultimate polyethylene matrix have a length of from about 100 microns to about three millimeters, and these fibers are selected to take a diameter of from about 5 to about 15 microns. Moreover, the morphology of the included graphitic carbon is important to the ultimate utility of the produced implant element; and graphitic carbon particles comprising lumps or flakes, rather than the disclosed fibers, have proved unsuitable for use as any substantial portion of the carbon amendment.

The finished implants may be subjected to gamma radiation at a dosage level of about 2.5 megarads prior to surgery and conveniently at the time of sterile packaging for commercial distribution.

One advantageous scheme for producing graphitic carbon fiber filaments for use in the present invention involves pyrolytic procedures wherein threads are spun of epoxy, phenolic or other suitable resin followed by incineration of the spun threads in an oxygen-free atmosphere to prevent the carbon from chemically combining with other elements. In order that the present invention may be more fully understood, a tibial plateau prosthesis, indicated generally by the reference numeral 60, is illustrated in FIGS. 6–8 inclusive. The tibial plateau prosthesis 60 is similar in many respects in overall shape and configuration to the tibial plateau prosthesis 20 previously described but differs in that it is fabricated as an ultra-high molecular weight polyethylene matrix 62 incorporating random length, graphitic carbon fibers 64 distributed in an unoriented array. Structurally, the prosthesis 60 comprises an implant body 66 having a semi-cylindrical sidewall 68 and a substantially straight, diametral sidewall 70 which interconnects the otherwise free ends of the sidewall 68. The body 66 is fashioned with a spherically concave upper surface 72, and the tibial plateau prosthesis 60 is further provided with a suitable number of pendant, locking prongs 74.

In repair of varus or valgus deformities of the tibia, the prosthesis 60 may be surgically embedded in a D-shaped cavity formed in the proximal end 76 of the tibia in general compliance with the corresponding disclosure involving the prosthesis 20; or, because of its high geometrical integrity, the prosthesis 60 may be installed in the proximal end of the tibia without an encircling rim of either bone or a combination of bone and synthetic bone cement, as is suggested in FIGS. 7 and 8. In such latter instances, the prongs 74 may be set in individual cavities 78 that have been excavated in the tibial bone tissue, using a quantity of bone cement 80.

After surgery and upon articulation of the repaired knee joint, the concave upper surface 72 of the prosthesis 60 will coact with a cooperating, metallic fermoral condyle 82 and act as a journal or bearing therefor, receiving the femoral condylar surface with sliding and rolling pressure therebetween.

In order to facilitate visual location of the otherwise substantially transparent prosthesis 60 in X-ray photographs of a knee joint having such an implant installed therein, an X-ray opaque member 84 is advantageously embedded in the body 66 of the prosthesis, as is best seen in FIG. 8. In compliance with the present invention, the member 84 is spaced inwardly from the surface of body 66 to exclude contact between the member 84 and body fluids whereby to minimize attendant hazards of chemical reaction or migration of substituent material. The member 84 may be fabricated from such radioopaque materials as stainless steel and alloys of cobalt and chromium.

While the present invention has been described with reference to a human body implant defining a tibial plateau prosthesis, it is to be recognized that the principles of the invention may be applied with equal advantage to elbow prostheses, hip prostheses and other body implants which, in use, undergo sliding, rolling or grinding pressures or combinations of such pressures. Accordingly, the drawings and the foregoing description are not intended to represent the only form of the invention in regard to the details of construction and manner of use. Changes in form and in the proportion of parts, as well as the substitution of equivalents, are contemplated as circumstances may suggest or render expedient; and although specific terms have been employed herein, they are intended in a generic and descriptive sense only and not for the purposes of limitation, the scope of the invention being delineated in the following claims.

The invention is claimed as follows:

1. A medical implant element which is to be subjected to rolling or sliding pressure or a combination of such pressures in the human body, comprising: a plurality of microparticles of ultra-high molecular weight polyethylene resin fused together into a matrix; and a quantity of graphitic carbon, consisting essentially of a substantially unoriented array of short, random length fibers, disposed in interstices of said matrix, said graphitic carbon fiber-containing matrix being a wear-resistant, substantially isotropic member.

2. A medical implant element according to claim 1 wherein said fibers have a length of from about 100 microns to about 3 millimeters.

3. A medical implant element according to claim 1 wherein said fibers have a diameter of from about 5 to about 15 microns.

4. A medical implant element according to claim 1 which further comprises an X-ray opaque member embedded therein spaced inwardly from the surface thereof.

5. A medical implant element according to claim 1 wherein the polyethylene molecules in said matrix are disposed in substantially random orientation.

6. A medical implant element according to claim 1 wherein said graphitic carbon is present in an amount of up to about 30 per cent by weight of said implant.

* * * * *